United States Patent
Bonrath et al.

(10) Patent No.: US 9,505,699 B2
(45) Date of Patent: Nov. 29, 2016

(54) PROCESS OF PRODUCTION OF DEHYDROLINALYL ACETATE (I)

(71) Applicant: DSM IP ASSETS B. V., Heerlen (NL)

(72) Inventors: Werner Bonrath, Basel (CH); Johannes Tschumi, Basel (CH); Fabrice Aquino, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/889,291

(22) PCT Filed: May 7, 2014

(86) PCT No.: PCT/EP2014/059363
§ 371 (c)(1),
(2) Date: Nov. 5, 2015

(87) PCT Pub. No.: WO2014/180915
PCT Pub. Date: Nov. 13, 2014

(65) Prior Publication Data
US 2016/0075632 A1    Mar. 17, 2016

(30) Foreign Application Priority Data

May 8, 2013 (EP) .................................. 13166960

(51) Int. Cl.
*C07C 67/08* (2006.01)
*C07C 69/145* (2006.01)
*B01J 31/02* (2006.01)
*B01J 31/26* (2006.01)

(52) U.S. Cl.
CPC ............ *C07C 67/08* (2013.01); *B01J 31/0225* (2013.01); *B01J 31/0232* (2013.01); *B01J 31/26* (2013.01)

(58) Field of Classification Search
CPC ..................................................... C07C 67/08
See application file for complete search history.

(56) References Cited

U.S. PATENT DOCUMENTS 2,797,235 A * 6/1957 Birbiglia ................. C07C 45/67
                                                    560/249
4,792,620 A * 12/1988 Paulik .................. B01J 31/0231
                                                    560/232

FOREIGN PATENT DOCUMENTS

CN    101 209 965    7/2008

OTHER PUBLICATIONS

Ishihara et al, Journal of Organic Chemistry, Scandium Trifluoromethanesulfonate as an Extremely Active Lewis Acid Catalyst in Acylation of Alcohols with Acid Anhydrides and Mixed Anhydrides, 1996, 61, pp. 4560-4567.*
Annotated PDF of Birbiglia et al (U.S. Pat. No. 2,797,235).*
Ishihara et al., "Scandium Trifluoromethanesulfonate as an Extremely Active Acylation Catalyst", *Journal of the American Chemical Society*, vol. 117, Jan. 1, 1995, two pages.
International Search Report for PCT/EP2014/059363 dated Jul. 14, 2014, two pages.

* cited by examiner

*Primary Examiner* — Paul A Zucker
(74) *Attorney, Agent, or Firm* — Nixon & Vanderhye P.C.

(57) ABSTRACT

The present invention is related to a novel and improved process for the production of dehydrolinalyl acetate (DLA), which IUPAC name is acetic acid 1-ethynyl-1,5-dimethyl-hex-4-enyl ester, starting from dehydrolinalool (DLL), which IUPAC name is 3,7-dimethyloct-6-en-1-yn-3-ol, by catalytic acetylation.

10 Claims, No Drawings

PROCESS OF PRODUCTION OF DEHYDROLINALYL ACETATE (I)

This application is the U.S. national phase of International Application No. PCT/EP2014/059363 filed 7 May 2014 which designated the U.S. and claims priority to EP Patent Application No. 13166960.8 filed 8 May 2013, the entire contents of each of which are hereby incorporated by reference.

The present invention is related to a novel and improved process for the production of dehydrolinalyl acetate (DLA), which IUPAC name is acetic acid 1-ethynyl-1,5-dimethyl-hex-4-enyl ester, starting from dehydrolinalool (DLL), which IUPAC name is 3,7-dimethyloct-6-en-1-yn-3-ol, by catalytic acetylation.

Dehydrolinalyl acetate (compound of formula (I))

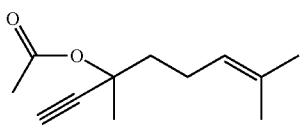
(I)

is an important and valuable compound for the use in the field of flavour and fragrance applications.

DLA can also be used in the production of linalylacetate (compound of formula (IV))

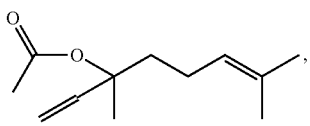
(IV)

which is also an important and valuable compound for the use in the field of flavour and fragrance applications.

Nowadays, DLA is usually produced by an acetylation of DLL by using p-toluene sulfonic acid as an "organic-soluble" acid catalyst.

In course of this reaction significant amounts of side products, such as D,L-iso-3,7-dimethyl-7-octen-1-in-3-yl acetate (iso-DLA; compound of formula (V)),

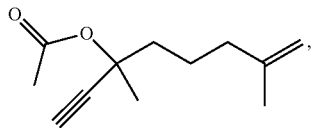
(V)

2,2,6-trimethyl-6-ethynyltetrahydropyrane (ETTP; compound of formula (VI))

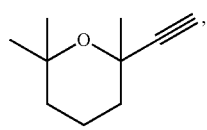
(VI)

and 3-isopropenyl-1-methyl-2-methylene-cyclopentylacetate (compound of formula (VI))

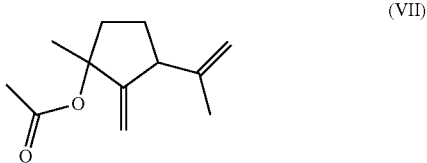
(VII)

are formed.

The goal of the present invention was to find an improved process for the production of DLA, without the above mentioned disadvantages of the process of the prior art (especially reducing the amount of the side products).

Surprisingly it was found that when a very specific type of catalyst is used, DLA is obtained by the acetylation of DLL with a significantly lower amount of undesired side products and with excellent selectivity and yield.

Therefore the present invention is related to the process of production of DLA, which is the compound of formula (I)

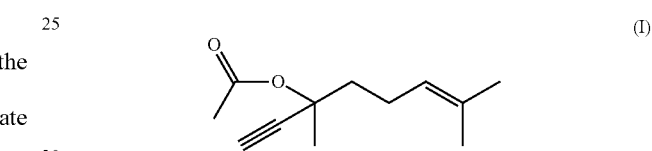
(I)

by reacting DLL, which is the compound of formula (II)

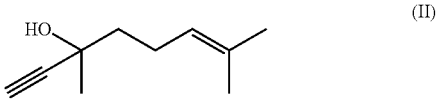
(II)

with acetic anhydride, which is the compound of formula (III)

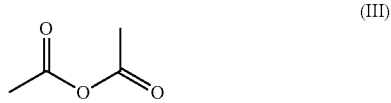
(III)

characterized in that the process is carried in the presence of at least one catalyst of formula (VIII)
wherein

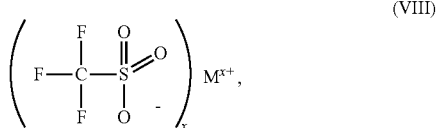
(VIII)

M signifies a 3d element or a 4f element from the periodic table and x is 2, 3 or 4.

3d elements comprise 10 chemical elements with atomic numbers 21 through 30 (from scandium through zinc).

4f elements are lanthanoide elements and comprise fifteen metallic chemical elements with atomic numbers 57 through 71 (from lanthanum through lutetium).

Preferred are catalysts of formula (VIII), wherein M is Sc, wherein x is 3 or Zn wherein x is 2.

In the process according to the present invention the catalyst (or the mixture of catalyst) is usually used in very low amount. Usually it is used in a ratio of 1000:1 up to 100,000:1 (compound of formula (II): catalyst). Preferably the ratio of compound (II) to catalyst is 10,000:1 up to 50,000:1.

The process according to the present invention is usually carried out at elevated temperatures.

Preferably the process according to the present invention is carried out at a temperature of 30-70° C., more preferably 30-60° C.

The process according to the present invention is usually carried out at normal pressure.

DLL and acetic anhydride ($Ac_2O$) can be added to the reaction mixture in equimolar amounts. It is also possible to use slight excess of either one of the compounds. Usually the acetic anhydride is used in a slight excess in regard to DLL. Preferably acetic anhydride (compound of formula (III)) is added in a ratio of 1:1 up to 3:1 (in regard to compound of formula (II)). More preferably acetic anhydride (compound of formula (III)) is added in a ratio of 1.1:1 up to 2:1 (in regard to compound of formula (II)).

The process according to the present invention is usually carried out without any solvent(s). But it would also be possible to use an inert solvent (or mixture of inert solvents).

Preferably the process according to the present invention is carried out without any solvents.

The starting material (compound of formula (II) and compound of formula (III)) can be mixed together before the process is started or one of the starting material can be added to the other while the process is going on.

Usually the compound of formula (II) and the catalyst are mixed and then the compound of formula (III) is added to the reaction mixture during a period of time.

After the addition and mixture of all the starting material the reaction mixture is let reacted for some time.

Usually the reaction time for the process according to the present invention is between 2 to 10 hours.

At the end of the reaction, the reaction mixture is usually neutralized and the remaining acetate anhydride and the acetic acid (product of the process) are removed from the reaction solution. This is usually done by distillation (normal pressure or at a reduced pressure).

The DLA which is obtained by the process according to the present invention can be used as such (flavour and fragrance applications) or it can be used in the production of other useful compounds, especially linanylacetate (obtained by hydrogenation of DLA).

The following examples serve to illustrate the invention. If not otherwise stated all parts are given are related to the weight and the temperature is given in ° C.

EXAMPLES

Example 1

Zn Triflate as Catalyst

Into a 350 ml four necked round bottomed flask fitted with a thermometer and a reflux condenser 162.2 g DLL (1.06 mol) and 15.3 mg of Zinc trifluoromethane sulfonate (0.042 mmol) were placed. Within 1 h, 120 ml (1.27 mol) $Ac_2O$ were added under stirring.

The yellowish reaction solution was heated to 45° C. (oil temperature), the reaction temperature increased until 50° C., after 8 h the reaction mixture was neutralized with 0.5 g sodium carbonate, cooling to room temperature. The $Ac_2O$ and AcOH-mixture was distilled at 150 mbar at 75° C.

211.3 g a yellowish liquid was obtained and contained 1.6 w % DLL, 0.3 w % iso-DLA, 92.6 w % DLA, 0.2 a % AcOH and 0.7 a % $Ac_2O$.

Total conversion: 97.9% and total yield: 95.6%.

Example 2

Sc Triflate as Catalyst

The same reaction conditions were used. But instead of Zinc trifluoromethane sulfonate Sc trifluoromethane sulfonate was used.

Total conversion: 91.6% and total yield: 87.9%. (only 0.1 wt-% of iso-DLA was obtained).

Other catalysts were tested

Pyridine, $H_3PO_4$, $H_2SO_4$, $CH_3SO_3H$, $(CF_3SO_3)_2O$, $CF_3SO_3H$, $(CF_3SO_3)_2Mg$, $CF_3SO_3Ag$ and $(CF_3SO_3)_2Ca$.

None of these catalysts have shown the same properties in the reaction as the catalyst according to the present invention.

The invention claimed is:
1. A process for the production of dehydrolinalyl acetate (DLA) which is a compound of formula (I):

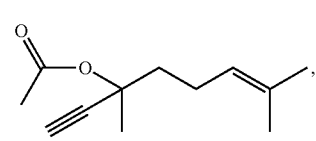

(I)

wherein
the process comprises reacting dehydrolinalool (DLL) which is a compound of formula (II):

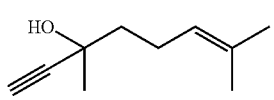

(II)

with acetic anhydride which is a compound of formula (III):

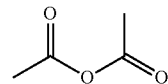

(III)

in the presence of at least one catalyst of formula (VIII):

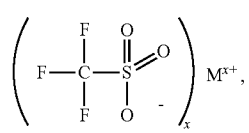

(VIII)

wherein
M is Zn and x is 2 or M is Sc and x is 3.

2. The process according to claim 1, wherein the DLA and the catalyst are present in a ratio of DLA to catalyst of 1000:1 up to 100,000:1.

3. The process according to claim 1, wherein the process is carried out at a temperature of 30-70° C.

4. The process according to claim 1, wherein the process is carried out at normal pressure.

5. The process according to claim 1, wherein the DLL and the acetic anhydride are present in a ratio of the acetic anhydride to DLL of 1:1 up to 3:1.

6. The process according to claim 1, wherein the process according is carried out in the absence of solvents.

7. The process according to claim 1, which further comprises neutralizing a reaction mixture containing the DLA and removing any remaining acetate anhydride and the acetic acid from the reaction mixture.

8. The process according to claim 2 wherein the ratio of DLA to catalyst is 10,000:1 up to 50,000:1.

9. The process according to claim 3, wherein the process is carried out at a temperature of 30-60° C.

10. The process according to claim 5, wherein the ratio of acetic anhydride to DLL is 1.1:1 up to 2:1.

\* \* \* \* \*